US006231583B1

(12) United States Patent
Lee

(10) Patent No.: US 6,231,583 B1
(45) Date of Patent: *May 15, 2001

(54) CORNEAL CIRCULAR CHANNEL DISSECTING DEVICE

(76) Inventor: Joseph Y. Lee, 11435 Via Lido, Loma Linda, CA (US) 92354

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/112,857

(22) Filed: Jul. 9, 1998

Related U.S. Application Data
(60) Provisional application No. 60/052,028, filed on Jul. 9, 1997.

(51) Int. Cl.$^7$ ........................................ A61F 9/00
(52) U.S. Cl. ...................... 606/166; 606/161; 606/170; 606/151; 623/4; 623/5
(58) Field of Search .................................. 606/166, 161, 606/107, 170, 151, 48, 49, 50; 623/4–5

(56) References Cited

U.S. PATENT DOCUMENTS

| | | | |
|---|---|---|---|
| 4,298,004 | 11/1981 | Schachar et al. | 128/305 |
| 4,452,235 | 6/1984 | Reynolds | 128/1 R |
| 4,607,617 | 8/1986 | Choyce | 128/1 R |

(List continued on next page.)

FOREIGN PATENT DOCUMENTS

| | | | |
|---|---|---|---|
| 388746 | 7/1973 | (RU) | 31/16 |

OTHER PUBLICATIONS

McCarey, B. et al., "Refractive Keratoplasty with Intrastromal Hydrogel Ienticular Implants," Assoc. For Res. In Vis. And Ophthal., Inc., vol. 21, No. 1, Part 1, Jul. 1981, pp. 107–115.

Beekhuis, W.H. et al., "Hydration Stability of Intracorneal Hydrogel Implants," Investigative Ophthalmology & Visual Science, vol. 26, Nov. 1985, pp. 1634–1636.

Beekhuis, W.H. et al., "Hydrogel Keratophakia: A Microkeratome Dissection in the Monkey Model," British Journal of Ophthalmology, 1986, pp. 192–198.

McCarey, B. et al., "Refractive Keratoplasty in Monkeys Using Intracorneal Lenses of Various Refractive Indexes," Arch Ophthalmol, vol. 105, Jan. 1987, pp. 123–126.

(List continued on next page.)

Primary Examiner—Michael Buiz
Assistant Examiner—Lien Ngo
(74) Attorney, Agent, or Firm—McCutchen, Doyle, Brown & Enersen, LLP

(57) ABSTRACT

This invention is a surgical device for producing a circular, interlamellar channel within the corneal stroma. An intracorneal ring can be implanted into this channel at the corneal periphery modifying the corneal curvature while sparing the important central optical zone of the cornea. This channel is formed by the sequential use of two separate instruments. The first instrument, the channel-guide dissector, is a circular dissecting instrument which is a split ring dissector with the dissecting end having a blunt tip and the other end connected to a handle. The important aspect of this channel-guide dissector is that it has a relatively narrow width which results in production of a lamellar corneal channel that is typically too narrow for the insertion of a typical intracorneal ring for myopic adjustment.

18 Claims, 4 Drawing Sheets

U.S. PATENT DOCUMENTS

| | | | |
|---|---|---|---|
| 4,624,669 | 11/1986 | Grendahl | 623/5 |
| 4,655,774 | 4/1987 | Choyce | 623/5 |
| 4,688,570 | 8/1987 | Kramer et al. | 128/305 |
| 4,815,463 | 3/1989 | Hanna | 128/305 |
| 4,834,750 | 5/1989 | Gupta | 623/6 |
| 4,941,093 | 7/1990 | Marshall | 364/413.01 |
| 4,961,744 | 10/1990 | Kilmer et al. | 606/166 |
| 4,976,719 | 12/1990 | Siepser | 606/151 |
| 5,090,955 | 2/1992 | Simon | 604/51 |
| 5,123,921 | 6/1992 | Werblin et al. | 623/5 |
| 5,188,125 | 2/1993 | Kilmer et al. | 128/898 |
| 5,236,970 | 8/1993 | Christ et al. | 523/113 |
| 5,300,118 | 4/1994 | Silvestrini et al. | 623/5 |
| 5,312,424 | 5/1994 | Kilmer et al. | 606/151 |
| 5,318,047 | 6/1994 | Davenport et al. | 8/632 |
| 5,331,073 | 7/1994 | Weinschenk, III et al. | 526/264 |
| 5,372,580 | 12/1994 | Simon et al. | 604/22 |
| 5,391,201 | 2/1995 | Barrett et al. | 623/5 |
| 5,403,335 * | 4/1995 | Loomas et al. | 606/161 |
| 5,405,384 | 4/1995 | Silvestrini | 623/5 |
| 5,466,260 | 11/1995 | Silvestrini et al. | 623/5 |
| 5,480,950 | 1/1996 | Wang et al. | 526/258 |
| 5,505,722 | 4/1996 | Kilmer et al. | 606/1 |
| 5,547,468 | 8/1996 | Simon et al. | 604/21 |
| 5,607,437 | 3/1997 | Simon et al. | 606/166 |
| 5,693,092 | 12/1997 | Silvestrini et al. | 623/5 |
| 5,733,334 * | 3/1998 | Lee | 606/166 |

OTHER PUBLICATIONS

Beekhuis, W.H. et al., "Complications of Hydrogel Intracorneal Lenses in Monkeys," Arch Ophthalmol, vol. 105, Jan. 1987, pp. 116–122.

Fleming, J. et al., "The Intrastromal Corneal Ring: Two Cases in Rabbits," Journal of Refractive Surgery, vol. 3, No. 6, Nov./Dec. 1987, pp. 227–232.

Climenhaga, H. et al., "Effect of Diameter and Depth on the Response to Solid Polysulfone Intracorneal Lenses in Cats," Arch Ophthalmol, vol. 106, Jun. 1988, pp. 818–824.

Burris, T. et al., "Effects of Intrastromal Corneal Ring Size and Thickness on Corneal Flattening in Human Eye," Refractive & Corneal Surgery, vol. 7, Jan./Feb. 1991, pp. 46–50.

Simon, G. et al., "Refractive Remodeling of the Cornea by Intrastromal Rings," Abstracts, Eighth International Congress of Eye Research, The International Society of Eye Research, Sep. 1988.

Burris, T. et al., "Flattening of Central Corneal Curvature with Intrastromal Corneal Rings of Increasing Thickness: An Eye–Bank Eye Study," J Cataract Refract. Surg., vol. 19, 1993, pp. 182–187.

Elander, R. et al., "Principles and Practice of Refractive Surgery," W.B. Saunders Company, including Chap. 21, Alloplastic Materials in Lamellar Surgery, by McCarey, Chap. 39, Synthetic Epikeratoplasty, by Thompson et al., Chap. 40, Intrastromal Corneal Ring, by Schanzlin et al., 1997.

Azar, D., "Refractive Surgery," Appleton & Lange, including Chap. 15, Corneal Biomechanics in Refractive Surgery, by Hjortdal, Chap. 27, The Intrastromal Corneal Ring for the Correction of Myopia, by Verity et al., Chap. 28, Intracorneal Alloplastic Inclusions, by Khoury et al., 1997.

Barraquer, J., "Basis of Refractive Keratoplasty," Refractive & Corneal Surgery, vol. 5, May/Jun. 1989, pp. 179–193.

Blavatskaia, E.D., "The Use of Intralamellar Homoplasty in Order to Reduce Refraction of the Eye," Arch. Soc. Ophthalmol. Optom., vol. 6, 1988.

Harr, D., "KeraVision Begins Implanting Corneal Reshaping Device in Blind Eyes," Refractive & Corneal Surgery, vol. 7, Sep./Oct. 1991, p. 343.

Simon, G. et al., "Gel Injection Adjustable Keratoplasty," Graefe's Arch Clin Exp. Ophthalmol, 1991, pp. 418–425.

Simon, G. et al., "Modification, Calibration, and Comparative Testing of an Automated Surgical Keratometer," Refractive & Corneal Surgery, vol. 7, Mar./Apr. 1991, pp. 151–160.

Thompson, K. et al., "Emerging Technologies for Refractive Surgery: Laser Adjustable Synthetic Epikeratoplasty," Refractive & Corneal Surgery, vol. 5, Jan./Feb. 1989, pp. 46–48.

Thompson, K., "Will the Excimer Laser Resolve the Unsolved Problems with Refractive Surgery?", Refractive & Corneal Surgery, vol. 6, Sep./Oct. 1990, pp. 315–317.

* cited by examiner

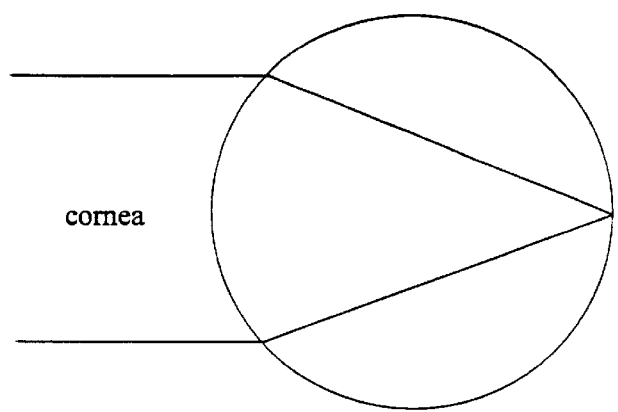
FIG. 1
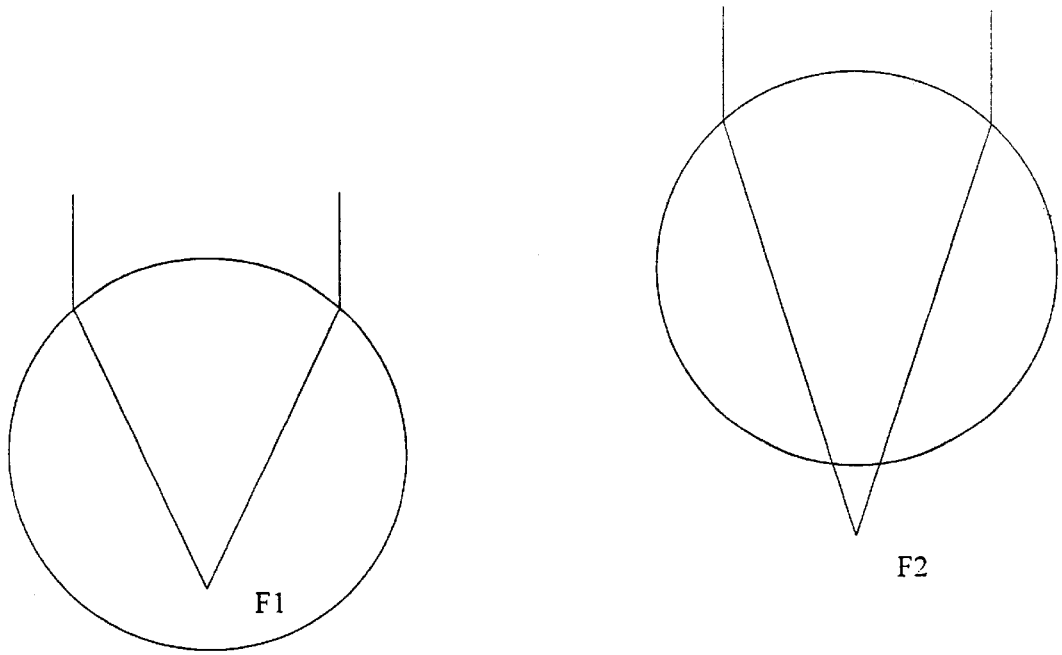
FIG. 2
FIG. 3

CORNEAL CIRCULAR CHANNEL DISSECTING DEVICE

CROSS-REFERENCE TO RELATED APPLICATIONS

This application claims the benefit of U.S. Provisional Application No. 60/052,028 which was filed Jul. 9, 1997.

BACKGROUND OF THE INVENTION

This invention is a surgical device for producing a circular, interlamellar channel within the corneal stroma. An intracorneal ring can be implanted into this channel at the corneal periphery modifying the corneal curvature while sparing the important central optical zone of the cornea. This channel is formed by the sequential use of two separate instruments. The first instrument, the channel-guide dissector, is a circular dissecting instrument which is a split ring dissector with the dissecting end having a blunt tip and the other end connected to a handle. The important aspect of this channel-guide dissector is that it has a relatively narrow width which results in production of a lamellar corneal channel that is typically too narrow for the insertion of a typical intracorneal ring for myopic adjustment.

However, the narrow channel produced serves as a guide for the introduction of the second instrument, also a lamellar dissecting instrument. The unique feature of this instrument is the design of the leading tip of this device. This leading tip is similar in shape to the tip of the first instrument and thus serves to guide the second instrument into the previously formed channel. Behind the leading tip is a wider flat blade that is gradually swept posteriorly, similar to a wing. The leading portion of this wing acts as the dissecting portion of the second instrument, also referred to as the winged dissector.

Ametropia, an undesirable refractive state of the eye, has three main subdivisions: myopia, hyperopia, and astigmatism. In myopia, by far the most common type of ametropia, the parallel light rays 20 which enter the eye as shown in FIG. 1 come to a focus F1 in front of the retina 24 as shown in FIG. 2. In hyperopia, the rays of light 20 come to a focus F2 behind the retina 24 as shown in FIG. 2. When the rays of light converge to not one, but several foci, it is referred to as astigmatism, in which condition the various foci may all lie before the retina; all lie behind the retina; or partly before the partly behind the retina.

Controversy has always surrounded the use of surgical procedures to correct refractive errors of the eye. Because of the risks inherent in surgical intervention, some has argued that no refractive error correctable by spectacles or contact lenses warrants such procedures. Until an ideal refractive procedure is developed, disagreement will persist among ophthalmologists as to which eyes and which patients are appropriate for refractive surgery. The ideal keratorefractive procedure for the correction of myopia should permit all the advantages of eyeglasses or contact lenses, namely, being able to correct a wide range of refractive errors, generating a high degree of predictability and stability such that <95% of patients achieve 20/20 uncorrected acuity with long-term stability, allowing reversibility or adjustability in the event that the refractive state of the eye changes, being extremely safe with minimal risk of adverse effects on the quality of vision and being cost effective. The refractive procedure should also have a favorable learning curve. If a technique permits only a small percentage of ophthalmologists to perform and achieve excellent visual results, it is a seriously deficient procedure.

For over a century, ophthalmologists have searched for a surgical method to permanently correct refractive errors. Over 15 different techniques have been developed and considerable experience gained in both animal and human models. Oftentimes a given refractive surgical technique has unsolved problems such as poor predictability, unstable refractive outcomes, adverse effects on the quality of vision, lack of adjustability and irreversibility. Poor predictability remains the largest unsolved problem in refractive corneal surgery. The main factors that contribute to poor predictability are: ) 1 variations and inaccuracies inherent with manual surgical techniques and 2) the variable would healing response to the surgery. Photorefractive keratectomy offers the possibility of reducing the surgical variability of the procedure. However, the variable corneal wound healing response affects the results of photorefractive keratectomy manifesting as regression of refractive effect which can be up to several diopters in amplitude.

For years it has been thought that refractive surgery with intracorneal implants could be used in the correction of myopia or hyperopia. Early techniques included lamellar removal or addition of natural corneal stromal tissue. These techniques required the use of a microkeratome to remove a portion of the cornea followed by lathing of either patient's or donor's removed cornea. The equipment is complex, the surgical techniques difficult, and most disappointingly, the results quite variable. The current trend in keratorefractive surgery has been toward techniques that are less traumatic to the cornea, that minimally stimulate the wound healing response, and behave in a more predicable fashion. the use of alloplastic intracorneal lenses to correct the refractive state of the eye, first proposed in 1949 by Jose Barraquer, have been plagued with problems of bicompatibility, permeabilty of nutrients and oxygen, etc.

More recent techniques have focused on minimizing the effects of the wound healing response by avoiding the central cornea. There have been multiple attempts to alter the central corneal curvature by surgically manipulating the peripheral cornea. These reply upon mechanisms first elucidated by J. Barraquer. Since 1964, "it has been demonstrated that to correct myopia, thickness must be subtracted from the center of the cornea or increased in its periphery, and that to correct hyperopia, thickness must be added to the center of the cornea or increased in its periphery." D. S. Zhivotosvskii, in USSR patent No. 3,887,846, describes an alloplastic, flat, geometrically regular, annular ring for intracorneal implantation of a diameter that does not exceed the diameter of the pupil. Refractive correction is accomplished primarily by making the radius of curvature of the surface of the ring larger than the radius of curvature of the surface of the recipient's cornea in order to achieve flattening of the central area of the cornea. The principle is simply that either insertion of an intracorneal ring in the corneal periphery or injection of gels is a preformed peripheral circumferential channel will induce flattening of the center of the cornea. Qualitatively, the same effect may be induced by a rigid ring in a gel. the addition of matter in the corneal periphery will induce an outward bulging of the corneal surfaces around the implant, thus incorporating excess corneal arc length. Consequently, less of the corneal arc will be available for covering the central cornea, which therefore must flatten.

Intracorneal rings have several advantages over photorefractive keratectomy (PRK) including leaving the central cornea intact, reversibility, rapid and stable effect and minimal wound healing responses. However, predictability is still an issue and there is no simple way of adjusting the refractive outcome, aside from explanting the intracorneal ring and replacing with another ring of different size. Methods of adjusting an intracorneal ring after the ring has been implanted in a simple, minimally invasive, predictable fashion have been described. This method is described more fully by J. Lee in U.S. Pat. No. 5,733,334, which disclosure is incorporated herein by reference.

If the adjustable corneal ring is shown to be truly adjustable in a discrete fashion, then it would meet many of the criteria for an ideal refractive procedure. Safety of the surgical procedure is still an issue. Current methods of producing a peripheral intrastromal lamellar channel within the cornea rely upon certain biomechanical properties of the cornea. At a central corneal thickness of 0.50 mm, the corneal elastic stiffness is approximately 49 kPa. However, the cornea shows very little resistance to shear deformation in the plane tangential to the surface. In shearing experiments, the shear stiffness has been found to be approximately 2 kPa. Thus a blunted circular blade can travel in a lamellar plane, separating the layers to form an interlamellar channel. In contrast, a sharp circular blade will not stay in an interlamellar channel and can more easily completely penetrate the cornea entering the anterior chamber. This is not a desirable outcome.

Methods for producing an interlamellar channel have been described. Simon in U.S. Pat. No. 5,090,955 describes a flat corkscrew delaminator which is used to carve a circular canal between the two corneal lamellae in which a gel such as a silicon gel is subsequently injected. The corkscrew delaminator consists of a flat wire about 1 mm or less in width and its edges are blunt or rounded as is its end.

A. E. Reynolds in U.S. Pat. No. 4,452,235 also describes a split-ring shaped dissecting member designed to produce a peripheral interlamellar corneal channel to permit implantation of an interacorneal ring.

There is, however, still a risk of corneal perforation into the anterior chamber with lamellar dissecting devices even with a blunted tip. Thus, there remains a need for a method to decrease the risk of perforating the cornea while producing a lamellar channel, especially in light of the fact that refractive surgery procedures today are almost universally an elective procedure.

There are several problems with currently used corneal delaminators. One problem is that if the dissecting tip is too sharp the delaminator or dissector may not stay in the interlamellar space but cut across lamellae resulting in a channel with uneven depth or at worst, perforate through Descemet's membrane into the anterior chamber of the eye. The blade may drift more anterior as it follows the arcuate path and perforate anteriorly though Bowman's membrane. This problem was overcome by the discovery that a comparatively blunt but rounded device would provide an intrastromal channel with a fairly constant depth without crossing interlamellar layers. However, blunted dissectors have their share of problems as will be described.

Another problem is centration of the channel around the apex of the cornea. Centration is important in the final refractive result after intracorneal ring placement. Proper centration is required to avoid postoperative complications, like irregular astigmatism and glare, that may interfere with visual function. Because the tip of the delaminator is made blunt, there is resistance to the passage of the delaminator which can cause distortion of the cornea during the dissection and result in decentration of the produced circular channel. B. Loomis in U.S. Pat. No. 5,403,335 describes a combination of vacuum chambers, insert rings, and ridges within a vacuum chamber to prevent this twisting of the corneal surface during insertion of the dissecting blade.

Using a vacuum suction ring stabilizes the cornea and is necessary in lamellar refractive procedures. When greater stabilization of the cornea is required, the vacuum on the suction ring must be increased with concomitant rise in the intraocular pressure. Strong suction maintains the cornea but also causes high intraocular pressure. Current dissectors require more stabilization because their dissecting blades are made blunt. The danger of corneal perforation is aggravated when the high intraocular pressure is followed by a sudden decrease in intraocular pressure in the event of corneal perforation. The damage caused by this sudden decrease in pressure can range from just the perforation itself to more serious consequences, such as damage to the iris or the lens or even an expulsive hemorrhage. A sudden decrease in intraocular pressure from a perforating injury may cause the intraocular contents to expulse. Thus a procedure that can be performed with minimal suction, requiring minimal corneal stabilization, even if the cornea undergoes perforation is less likely to cause severe anterior segment damage.

Lastly, as the channel is being formed by the rotational movement of a given circular delaminator, the friction forces add resistance to the forward movement of the tip of the circular delaminator and the initial incision (1) perpendicular to the corneal surface is gaped open. Healing in this area can be complicated by tears from the shearing forces. One solution was to partially complete the channel by using a dissector in one direction followed by completion of the interlamellar channel by using another dissector which is rotated in the opposite direction. Complete rotation into the cornea of a dissector involves more resistance to forward direction and complications of tearing the initial incision than a partial rotation.

SUMMARY OF THE INVENTION

According to various embodiments of the invention, techniques and instruments are provided to overcome these problems and permit a continuous 360 degree channel to be formed with much more assurance of forming a circular channel that is centered around the apex, with less stress on the surrounding cornea and less risk of serious complications such as complete perforation of the cornea and Descemet's membrane. Even if the cornea is perforated, it is a much smaller perforation and less traumatic than that with current full-width delaminators because the blade width is more narrow and because less suction is required to stabilize the cornea during the procedure.

Accordingly, several objects and advantages of the invention are to provide circular corneal channel dissectors which obviate the disadvantages of prior dissectors by the sequential use of two dissectors as follows: a first instrument which is similar to prior dissectors but narrower in width with a blunted tip which allows forming a circular channel in the corneal periphery in an interlamellar fashion, which encounters less corneal resistance because of the smaller size thus allowing improved centration, which provides a guide channel for a second instrument that increases the width of the channel; and a second instrument which has a front portion that is a blunted dissector similar to prior dissectors but narrower in width followed by a portion that is wider with the wider portions having a sharp leading edge, which decreases the corneal resistance encountered by prior dissectors, which permits formation of smoother channel surfaces and less post-operative scarring, which diminishes the need for strong vacuum suction stabilization of the cornea and associated increased risk of severe operative complications, and which increases the likelihood of forming a circular channel that is centered around the corneal apex because of the decreased resistance.

Still further objects and advantages will become apparent from a consideration of the ensuing description and accompanying drawings.

DESCRIPTION OF THE DRAWINGS

FIG. 1 is a schematic representation of a horizontal section of the human eye;

FIG. 2 is a schematic representation showing how the light rays focus in front of the retina of the eye in the condition of myopia;

FIG. 3 is a schematic representation showing how light rays focus behind the retina of the eye in the condition of hyperopia;

DETAILED DESCRIPTION OF THE INVENTION

The present invention is a surgical device which provides a technique for producing a circular channel within the corneal stroma of the eye. It allows for the formation of an interlamellar channel within the corneal periphery while sparing the central cornea. The surgical technique uses two separate instruments: a channel-guide dissector which is a circular, split-ring dissector with the dissecting end having a slightly blunted tip which allows formation of a narrow lamellar channel and a second instrument which is a wing-shaped lamellar dissector with a tip shaped similarly to the channel-guide dissector thus allowing guidance of the dissecting wing portion into the narrow previously formed lamellar channel. The wing-shaped dissector forms a channel sufficiently wide to allow insertion of an intracorneal ring. The intracorneal ring placed within the created corneal channel alters the shape of the cornea and results in surgical correction of myopia.

This invention is a surgical device for producing a circular, interlamellar channel within the corneal stroma of the eye in anticipation of implanting an intracorneal ring to correct refractive errors.

Figure 4:
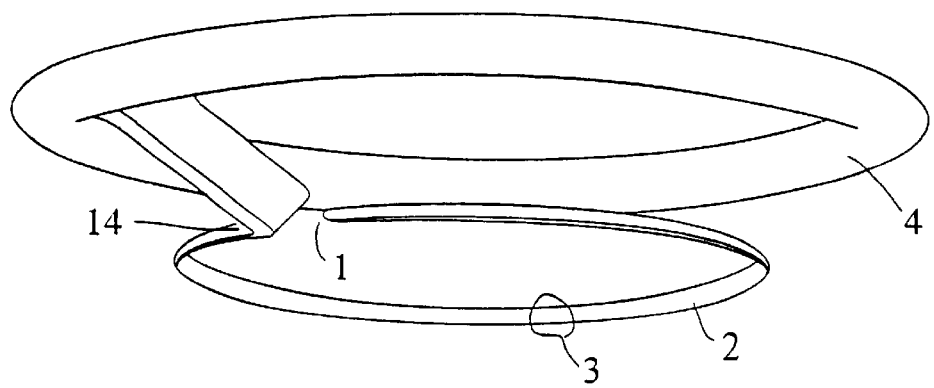
FIG. 4 is a perspective view of the guide-channel producing instrument of the invention.
Figure 5:
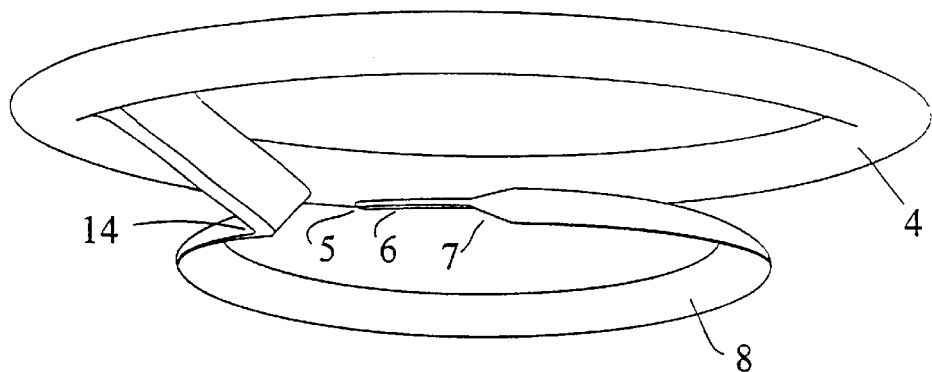
FIG. 5 is a perspective view of the winged instrument of the invention.
Figure 6:
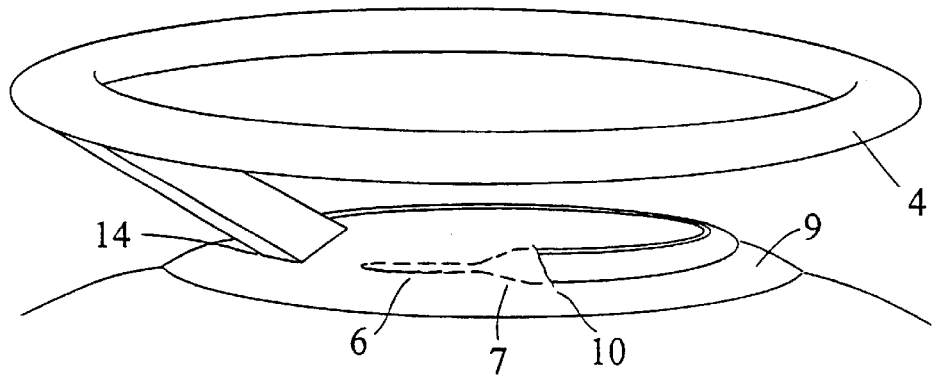
FIG. 6 is a perspective view of the winged instrument partially inserted into a cornea of an eye.
Figure 7:
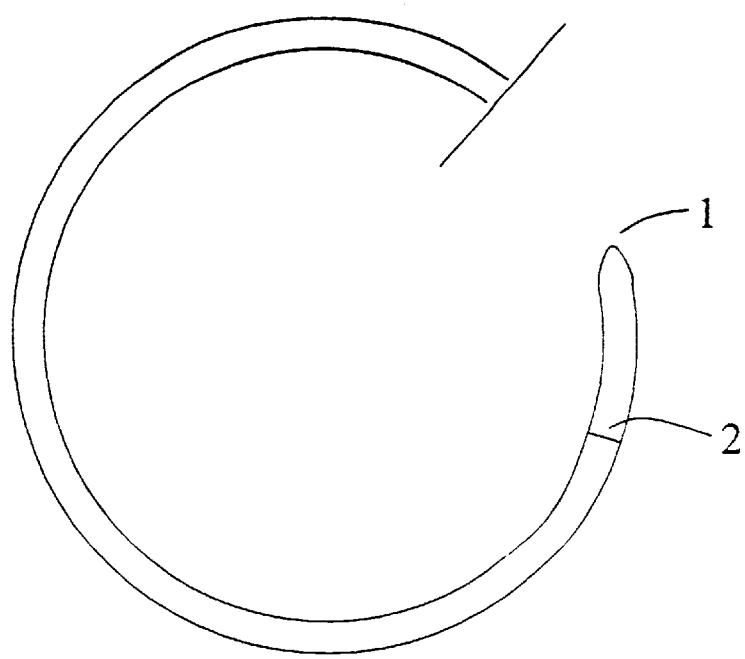
FIG. 7 is a plan view of the guide-channel producing instrument of the invention.

The first instrument, as illustrated in FIG. 4, is a circular channel-guide dissector that is similar to previous devices but of smaller width (2) and having a tapered blunt dissecting end (1). The cross-sectional shape (3) of the circular blade can be varied but ideally is more oval such that the strength of the device is maximized while minimizing the amount of surface area contacting the corneal stroma and thus also minimizing resistance. The cross-sectional shape can include hexagonals, squares, circles, and similar variations of those geometric shapes. The angle of the blade relative to the horizontal is approximately 35 degrees (+/−15 degrees) to correspond to the angle of the cornea at the periphery such that the dissector forms a channel parallel to the peripheral corneal lamellae. The blade is made of typical alloys or metals used in the production of surgical instruments and can include stainless steel and titanium. The surface of the instrument but not the dissecting tip may also be coated with Teflon to further decrease resistance. As shown in FIGS. 4–6, the instrument may have a handle and be used freehand. The instrument may also be used in combination with a suction ring system that stabilizes the cornea during the procedure. Visualization is much improved because of the open design of the dissector and handle.

The channel-guide dissector has the following dimensions: an outer diameter of the circular blade of 8.0 mm +/−2.0 mm; blade thickness of approximately 0.2 mm, with a preferred range between approximately 0.05 to 0.3 mm; width that is approximately 1.5 to 3 times larger in dimension than the thickness; the blade is also curved to about 385 degrees so that it is superimposed by 25 degrees.

The second instrument, as shown in FIG. 5, is also a lamellar dissecting device and is referred to as the wing-shaped dissector. It has a unique design that allows it to follow the small channel produced by the channel-guide device. The leading tip of the instrument (6) is fashioned to be similar in shape and size to the channel-guide dissector such that the tip of the winged dissector easily enters the small previously formed corneal lamellar channel produced by the guide-channel instrument. This leading tip is blunted and serves to guide the dissecting portion (7) of the winged instrument such that the circular pattern established by the channel-guide dissector is maintained. The leading tip may be made slightly larger in cross-sectional size than the guide-channel instrument to create a snug fit. Posterior to the leading tip of the second instrument, there is a wing shaped blade (7), such that the width is greater than the width of the guide tip (6) and sufficiently large to produce a widened channel adequate to allow placement of a corneal ring. Unlike the blunted tip, the leading edge of the wing or dissecting portion (7) is made to be as sharp as current microkeratome blades.

Figure 8A:
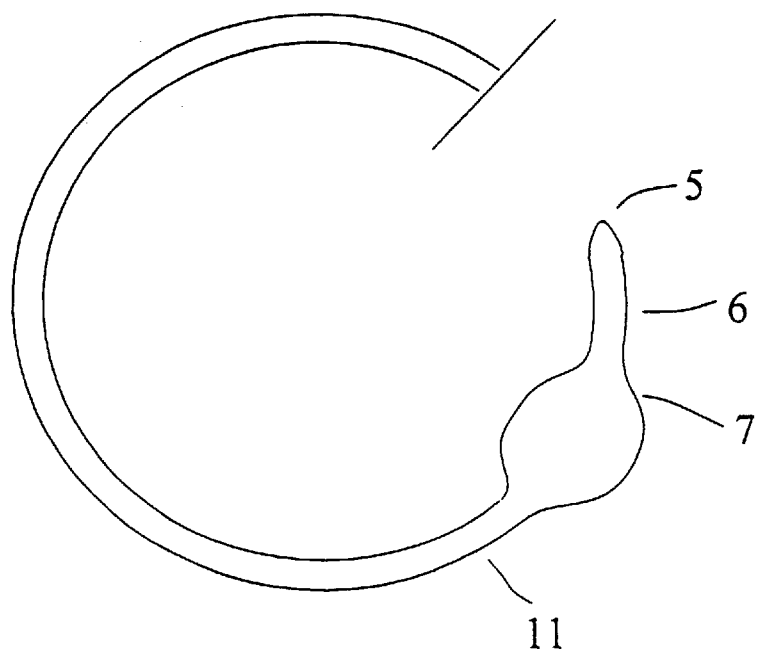
FIG. 8(a) is a plan view of a variation of the winged instrument of the invention.
Figure 8B:
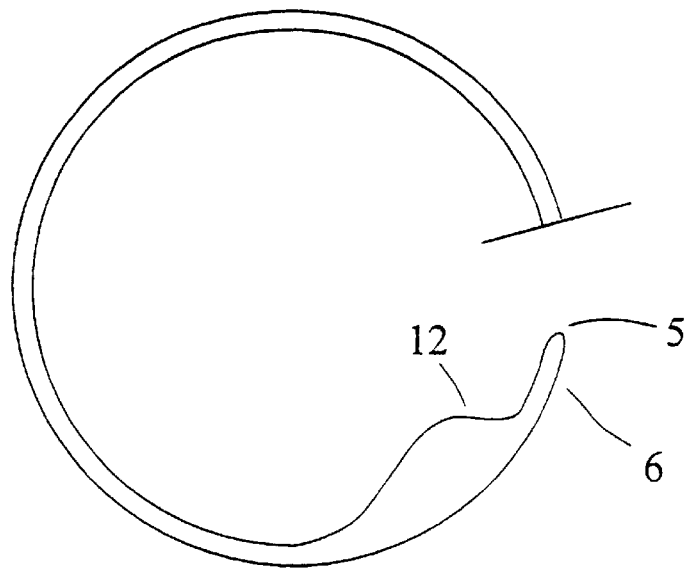
FIGS. 8(b) and 8(c) are also plan views of variations of the winged instrument.
Figure 8C:
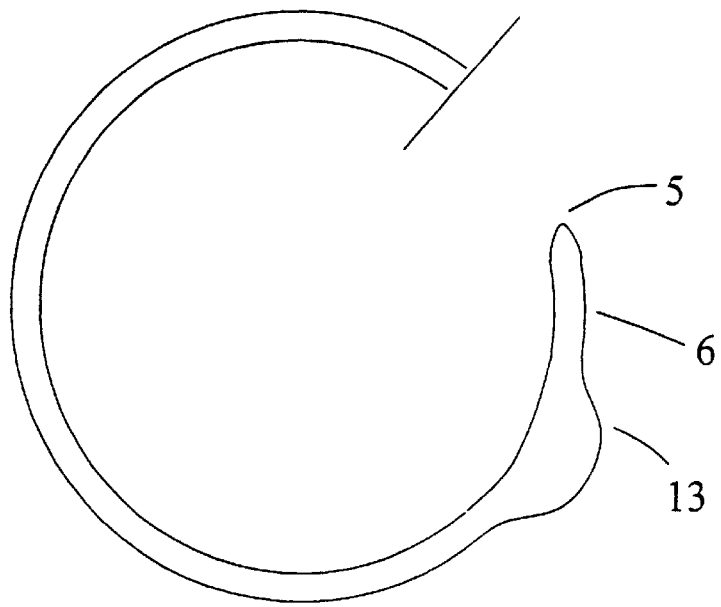

Referring to FIG. 5, the distance between the tip (5) and the leading edge of the blade (7) can be varied but in the ideal embodiment is approximately 10–20 arc degrees. The blade (8) is shown to be less than 360 degrees in length. In a variation, the length of the blade can be increased so that the distance from the attachment of the blade to the handle (4) to the leading edge of the blade (7) measures 360 degrees in length such that the blunted tip portion (6) is overlapped by a portion of the blade near the attachment to the handle. The leading edge of the sharp blade (14) arises from the side of leading guide tip and sweeps posteriorly. This widened portion of the instrument does not necessarily extend the rest of the length of the instrument as shown in FIG. 8(a). In various embodiments, the second instrument may have a wing only towards the inner diameter of the guide tip (12)(FIG. 8b) or a wing only towards the outer diameter of the guide tip (13)(FIG. 8c).

The procedure is begun by marking the corneal epithelial surface at the diameter the circular channel is desired with a circular marker. After the marker is soaked in a dye (usually gentian violet or brilliant green), it is placed on the cornea to obtain the mark. An incision (10) is made into the cornea perpendicular to the corneal surface, preferably radial (but can also be performed with a circumferential incision) at approximately ⅔ corneal depth. A Suarez spreader (Storz) is used to start a lamellar channel at the appropriate depth, usually ⅔ corneal depth. The channel-guide dissector is then used to form a small 360 degree annular intrastromal corneal channel, using the circular surface corneal mark to guide the instrument and form the circular channel. At this point, there is present in the cornea a small, circular, 360 degree interlamellar channel. This channel is too small to permit a corneal ring. A typical corneal ring has a width of approximately 0.9 mm. However, the channel will serve as a guide channel for the winged instrument which will enlarge the channel to a sufficient size to allow a corneal ring to be placed. Again, the advantages of this channel-guide dissector is that the channel is much more likely to be circular and centered around the apex of the cornea since it has a smaller cross-sectional size, thus minimizing resistance. If a lamellar dissecting device is attached to a suction ring, it can only take a given circular path in relation to the suction ring attachment and there may be an increased incidence of forming a channel that is not centered around the corneal optical center. Also, if the cornea distorts slightly as the lamellar dissecting device is forming the channel, the surgeon is unable to make an adjustment to alter the direction of the device if attached to a vacuum device. With the described first instrument, there is much less resistance because of the smaller width. The lamellar dissection may be accomplished free-hand, without the attachment to a suction ring. Also, because the instrument is relatively simple, there is a better view of the cornea through the microscope. Improved visualization allows the surgeon to more adeptly make any necessary adjustments. The surgeon can more easily anticipate impending perforation of the dissector through the cornea and thus prevent actual perforation. A suction ring may be attached to the surrounding conjunctiva to immobilize the eye, but the first instrument is not necessarily attached to it. With a free-hand dissection, the surgeon can more easily manipulate the direction of the tip and follow the circular surface corneal mark made prior to the dissection and thus obtain a more circular channel. Also, in the rare instance that the tip of the first instrument deviates from a lamellar dissection and perforates the cornea, the surgery can be discontinued with much less trauma incurred by the cornea, as compared to a larger dissecting device that attempts production of a full-size channel with one instrument. There is a definite theoretical risk of perforating the cornea during this lamellar dissection and this risk is increased with the greater force required in attempting to form a complete intrastromal channel with one pass. If this channel production can be made safer with less risk of serious complication, it is a definite advantage especially since myopic refractive surgery is typically an elective procedure.

The winged-channeling device is then advanced into the smaller channel previously formed. It is advanced until it has formed a 360 degree channel that is now substantially larger than the first guide channel and of adequate size to accommodate an intracorneal ring. The leading edge (7) of the dissecting wing may be much sharper than the tip of current circular lamellar dissecting devices. Current devices intentionally have a slightly blunted tip to maintain a lamellar dissection and thus prevent accidental penetration through the cornea into the anterior chamber of the eye. A blunted tip aids the instrument in staying within a lamellar plane. However, a blunted tip also adds resistance to the passage of the instrument through the corneal stroma and results in a channel that is not as smoothly formed compared to one made by a sharper instrument.

Microkeratomes are similar instruments in that they are designed to create a lamellar corneal flap. The keratome blades are extremely sharp and electron microscopic examination shows a very smooth surface. However, because the blades are so sharp, these instruments do not truly form pure lamellar dissections. Duller blades can affect the smoothness of the surface produced. Dull blades tend to scrape tissue and cut irregularly. These microkeratomes can be made very sharp because the instruments have a guard that usually sets the depth of the blade into the anterior cornea. Blades must be remarkably sharp and smooth to increase the depth consistency and smoothness. These sharp blades do not have to wholly rely upon the lamellar layers of the cornea to prevent perforation into the anterior chamber because of the presence of a guard plate that only allows the blade to cut at a certain corneal depth. The microkeratome has a high-speed oscillating blade that uses the principle of the carpenter's plane to resect corneal discs of different thicknesses. Variables such as the speed of passage of the microkeratome, pressure exerted by the surgeon's hands on the instrument, and intraocular pressure affect the thickness of corneal flap created by the microkeratome. Intraocular pressure must be at least 65 mm Hg for the resection.

Because of the nature of a circular lamellar channel, a guard plate to set thickness is not feasible. To overcome this problem and to assure that the circular lamellar blade stays at a certain pre-determined corneal depth, circular lamellar blades were blunted. It was noticed that—sharper circular blades cut across lamellae as would be expected with the risk of upward or downward deviation of the blade tip. But a dulled blade has a different set of problems including increased resistance to passage with resultant deformation of the cornea during dissection and a channel that has rougher surfaces.

In the described method, because a guide-channel is already present and because the second instrument has a guide-tip that takes advantage of the guide-channel to direct itself in the proper lamellar layer and direction, the dissecting wing portion of the winged dissector may be made much sharper than current circular lamellar blades, without the fear of the instrument becoming misdirected and accidentally completely perforating the cornea. The sharpness of the dissecting portion of the second instrument allows the production of a much smoother superior and inferior channel surface. The resistance to passage of the winged instrument is decreased because the channel is already partly formed. This resistance to passage is further decreased by the increased sharpness of the blade of the second instrument. The risk of perforation, although small, is greatest with the formation of the guide-channel. If there is perforation during the formation of the guide-channel, the damage incurred is less than that incurred with perforation resulting from current dissecting devices.

In an alternate method, the instrument may be passed only 180 degrees followed by a mirror-image of the winged-channeling instrument entering the same initial incision and completing the opposite 180 degrees. The advantage of using the winged-channeling instrument is that because a guide-channel is already formed, a 360 degree continuous channel encircling the apex is guaranteed and because a smaller channel already exists, less stress is exerted onto the cornea during the process of enlargement. If left-directed and right-directed winged-channelling instruments are each used to complete 180 degrees of the channel, then there is even less resistance encountered in forming the final channel. The left-directed instrument is rotated clockwise and the right-directed instrument rotated counter-clockwise. Normally frictional resistance increases much more towards the end of the 360 degree channel when using a typical helicoidal spatula type channelling device because of the added drag of the almost completely inserted instrument contacting the corneal stromal tissue. When using current 360 degree channelling devices having blunted tips, even with mirror-image instruments, one cannot initially produce a 180 degree channel clockwise and complete the 180 degree channel opposite with the mirror-image instrument and expect a continuous 360 degree channel because if such is undertaken, the channels will have formed between different interlamellar spaces such that the two channels will not be continuous.

In our inventive process, a guide channel is produced in a continuous fashion 360 degrees around the apex. With left and right-directed channelling instruments, the two channels will be in the same interlamellar plane and will meet at their respective ends at 180 degrees away from the initial incision site. It is virtually impossible to form 180 degrees of a channel in one direction followed by completion of the interlamellar channel by using another dissector which rotates in the opposite direction and expect the channel to be continuous. Even with initiation of the channel at a similar corneal depth in both directions, at the point where the two channels meet the channels will most likely be in slightly different lamellar layers. If two corneal ring segments are to be placed, this will not pose a problem. However, the point where the two channels meet in different lamellar layers will act as a barrier to impede the placement of a single split corneal ring.

In yet another method, the initial channel-guide dissector is not used prior to the winged instrument:

1. If a complete, continuous channel is desired, the tip of the winged instrument is placed within the initial ⅔ depth corneal incision and rotated 360 degrees. The tip of the winged instrument is blunt and creates a lamellar channel that is immediately followed by the sharper wing portion of the same instrument which acts to enlarge the guide channel created. The tip still serves to maintain the winged-instrument in a lamellar plane while the sharper wing reduces the resistance to passage compared to current blunted tip instruments. The advantage of this method compared to the previous methods described is that only one pass or rotation of an instrument is required. The disadvantage of this method is that there is greater resistance encountered with the passage of a winged instrument into an unoperated cornea compared to the resistance encountered into a cornea which has a guide-channel placed.

If a complete, continuous channel is not required such as in placement of corneal ring segments for the correction of astigmatism, right-going and left-going winged instruments are used to create each half of the lamellar channel in a cornea without the prior creation of a guide-channel.

Although the description above contains many specificities, these should not be construed as limiting the scope of the invention but as merely providing illustrations of some of the presently preferred embodiments of this invention. Various other embodiments and ramifications are possible within its scope.

What is claimed is:

1. A corneal lamellar dissecting device comprising:
   a handle; and
   a curved dissecting portion forming a split ring comprising:
      a rear end connected to the handle;
      a dulled leading end; and
      a blade portion positioned between the rear end and the dulled leading end and including at least one sharp blade edge which is wider than the dulled leading end and faces the dulled leading end.

2. The device as claimed in claim 1, whereby said device is composed of a metal.

3. The device as claimed in claim 1, wherein the ratio of the width of the dulled leading end and the width of the blade portion is between about 0.1:1 and 0.8:1.

4. The device as claimed in claim 1, wherein the curved dissecting portion is curved to about 180 degrees.

5. The device as claims in claim 1, wherein the curved dissecting portion is curved to about 360 degrees to 380 degrees.

6. The device as claim in claim 1, wherein the width of the dulled leading end ranges between 0.1 to 0.5 millimeters.

7. The device as claimed in claim 1, wherein the width of the blade portion ranges between 0.5 to 2 millimeters.

8. A method for forming a circular lamellar channel in the peripheral cornea of an eye comprising the steps of:
   making an incision into the peripheral corneal surface;
   forming an annular intralamellar guide channel;
   inserting a lamellar dissector along at least a portion of the guide channel to widen the channel and create at least a partial ring channel, the lamellar dissector comprising a dulled leading end and a sharp blade edge; and
   removing the lamellar dissector.

9. The method as in claim 8, wherein the intralamellar guide channel has a width of 0.1 to 0.5 millimeters.

10. The method as in claim 8, wherein the intralamellar guide channel is a continuous 360 degrees.

11. The method as in claim 8, wherein the lamellar dissector is comprised of:
   a rear end connected to a handle;
   a dulled leading end; and
   a blade portion positioned between the rear end and the dulled leading end and including at lease one sharp blade edge which is wider than the dulled leading end and faces the dulled leading end.

12. The method as in claim 8, wherein the lamellar dissector is curved to about 180 degrees.

13. The method as in claim 12, wherein the lamellar dissector is curved in a clockwise direction.

14. The method as in claim 12, wherein the lamellar dissector is curved in a counter-clockwise direction.

15. The method as in claim 8, wherein the guide channel is widened comprising the steps of:
   inserting at least partially a lamellar dissector in a clockwise fashion into the guide channel;
   removing the lamellar dissector;
   inserting at least partially a lamellar dissector in a counter-clockwise fashion into the guide channel; and
   removing the lamellar dissector.

16. The method as in claim 8, wherein the lamellar dissector is curved to about 360 degrees.

17. The method as in claim 8, wherein the width of the dulled leading end of the lamellar dissector ranges between 0.1 to 0.5 millimeters.

18. The method as in claim 8, wherein the width of the blade of the lamellar dissector ranges between 0.5 to 2 millimeters.

* * * * *